(12) United States Patent
Busaba

(10) Patent No.: US 6,369,725 B1
(45) Date of Patent: Apr. 9, 2002

(54) METHOD FOR BINARY TO DECIMAL CONVERSION

(75) Inventor: Fadi Y. Busaba, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/669,226

(22) Filed: Sep. 26, 2000

(51) Int. Cl.[7] .............................................. H03M 7/04
(52) U.S. Cl. ........................................ 341/84; 708/211
(58) Field of Search ...................... 341/84, 50; 708/211

(56) References Cited

U.S. PATENT DOCUMENTS 5,956,265 A * 9/1999 Lewis ......................... 364/757
6,282,554 B1 * 8/2001 Abdallah et al. ........... 708/204

* cited by examiner

Primary Examiner—Peguy JeanPierre
(74) Attorney, Agent, or Firm—Lynn Augspurger; Cantor Colburn LLP

(57) ABSTRACT

An exemplary embodiment of the invention is a method and system for converting a number from binary to decimal. The method includes obtaining an N-bit binary number and then determining the number of multiplications necessary to complete the conversion process by first determining the number of leading zeroes. The method then divides the N-bit number into 12-bit segments where each segment is represented as a binary coded decimal number. The method then multiplies at least one binary coded decimal number by a variable in response to the number of multiplications to determine the resulting decimal value.

14 Claims, 3 Drawing Sheets

| hex digits | (1. hex -> BCD) | (16.hex -> BCD) | (256.hex -> BCD) |
|---|---|---|---|
| 0000 | 0000 0000 0000 0000 | 0000 0000 0000 0000 | 0000 0000 0000 0000 |
| 0001 | 0000 0000 0000 0001 | 0000 0000 0001 0110 | 0000 0010 0101 0110 |
| 0010 | 0000 0000 0000 0010 | 0000 0000 0011 0010 | 0000 0101 0001 0010 |
| 0011 | 0000 0000 0000 0011 | 0000 0000 0100 1000 | 0000 0111 0110 1000 |
| 0100 | 0000 0000 0000 0100 | 0000 0000 0110 0100 | 0001 0000 0010 0100 |
| 0101 | 0000 0000 0000 0101 | 0000 0000 1000 0000 | 0001 0010 1000 0000 |
| 0110 | 0000 0000 0000 0110 | 0000 0000 1001 0110 | 0001 0101 0011 0110 |
| 0111 | 0000 0000 0000 0111 | 0000 0001 0001 0010 | 0001 0111 1001 0010 |
| 1000 | 0000 0000 0000 1000 | 0000 0001 0010 1000 | 0010 0000 0100 1000 |
| 1001 | 0000 0000 0000 1001 | 0000 0001 0100 0100 | 0010 0011 0000 0100 |
| 1010 | 0000 0000 0001 0000 | 0000 0001 0110 0000 | 0010 0101 0110 0000 |
| 1011 | 0000 0000 0001 0001 | 0000 0001 0111 0110 | 0010 1000 0001 0110 |
| 1100 | 0000 0000 0001 0010 | 0000 0001 1001 0010 | 0011 0000 0111 0010 |
| 1101 | 0000 0000 0001 0011 | 0000 0010 0000 1000 | 0011 0011 0010 1000 |
| 1110 | 0000 0000 0001 0100 | 0000 0010 0010 0100 | 0011 0101 1000 0100 |
| 1111 | 0000 0000 0001 0101 | 0000 0010 0100 0000 | 0011 1000 0100 0000 |

FIG.3

METHOD FOR BINARY TO DECIMAL CONVERSION

BACKGROUND OF THE INVENTION

The present invention relates generally to converting binary numbers to decimal numbers and in particular to an iterative method for converting binary numbers to decimal numbers.

Currently, computer systems performing binary to decimal conversions require many clock cycles for evaluating the binary number as a whole and, thus, increasing processing periods. The existing practice is inefficient, consumes a significant amount of time, and reduces system performance. Typically, the conversion from pure binary to binary coded decimal code is effected in several ways. For example, an adder-subtracter algorithm and a table of binary representations of the powers of 10 or powers of 10 multiplied by the numbers from 0 to 9 are used. The adder-subtractors may be that of a main arithmetic unit and may be wired or programmed to obtain the conversion. With the existing practices, the conversion time is fixed and therefore cannot be reduced.

Consequently, there is a need to speed up the binary to decimal conversion process and to reduce the number of clock cycles required to make the necessary conversions. Therefore, a quicker and more efficient method is desired.

BRIEF SUMMARY OF THE INVENTION

An exemplary embodiment of the invention is a method and system for converting a number from binary to decimal. The method includes obtaining an N-bit binary number and then determining the number of multiplications necessary to complete the conversion process by first determining the number of leading zeroes. The method then divides the N-bit number into 12-bit segments where each segment is represented as a binary coded decimal number. The method then multiplies at least one binary coded decimal number by a variable in response to the number of multiplications to determine the resulting decimal value.

BRIEF DESCRIPTION OF THE DRAWINGS

Referring now to the drawings wherein like elements are numbered alike in several FIGURES:

FIG. 3 depicts exemplary tables used in conversion of binary digits to binary coded decimal numbers.

DETAILED DESCRIPTION OF THE INVENTION

As discussed herein, currently binary numbers are converted to decimal numbers by utilizing adder-subtracter methods. One shortcoming of the existing practice is that the entire number to be converted must be evaluated as a whole. In other words, this makes the conversion time fixed and therefore it cannot be reduced. Highlighting the problem with the current practice is the inefficiency of executing a fixed number of clock cycles to make a binary to decimal conversion, thereby expending valuable processor time.

The present invention solves these problems by introducing a method that quickly converts a binary number into a decimal number by utilizing iterative evaluations of a particular number's leading zeroes. In addition, the number chosen for conversion is divided into three sections where each will be simultaneously evaluated. These evaluations determine the number of leading zeroes, and that number is used to set a counter to limit the maximum number of multiplications his process will require. Therefore, the present invention saves valuable processing time.

Figure 1:
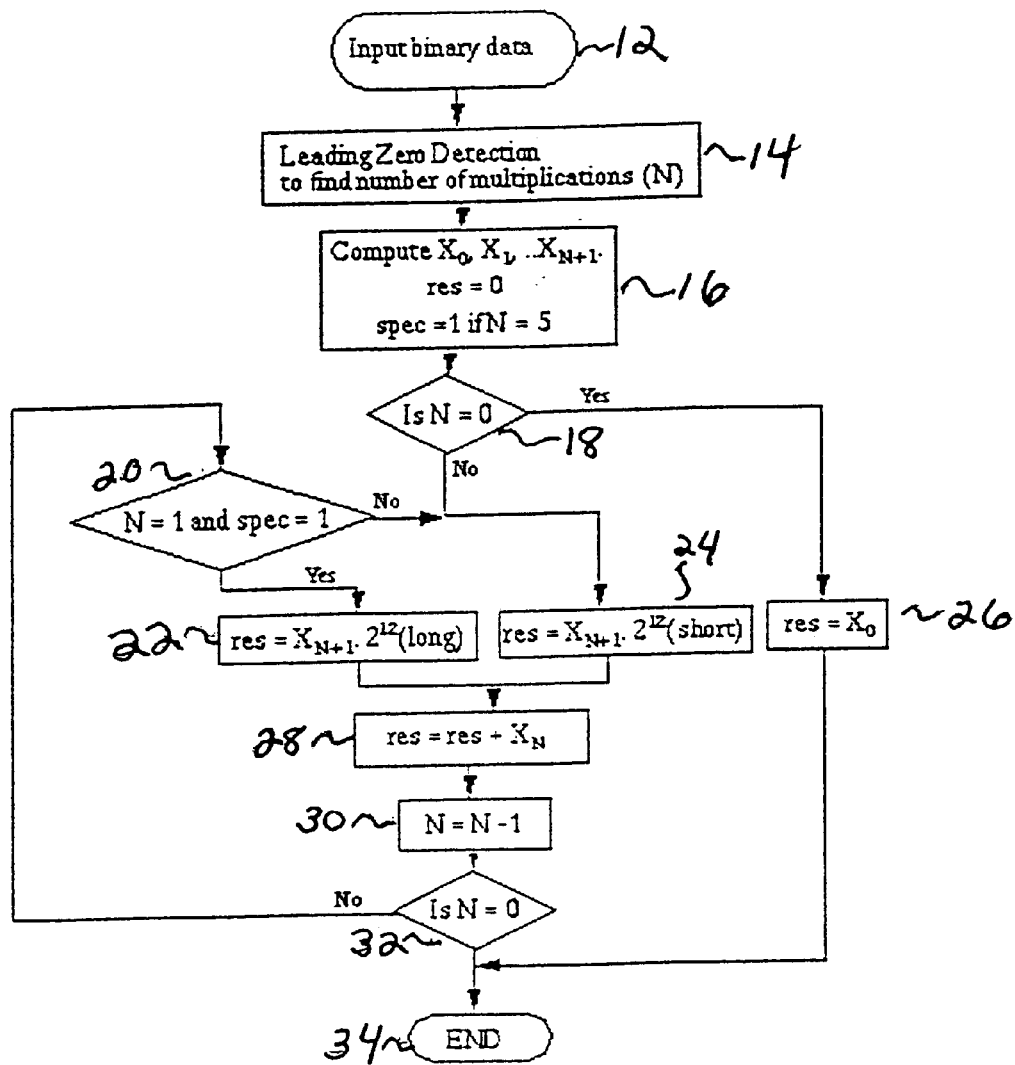
FIG. 1 is a flow chart of an exemplary embodiment of the invention.

FIG. 1 is an exemplary flow chart for the preferred embodiment of the invention for converting binary numbers into decimal numbers by using two main instructions referred to as CVD and CVDG. The CVD instructions convert a 32-bit binary number into a 64-bit decimal number, while the CVDG instructions convert a 64-bit binary number into a 128-bit decimal number. In either case, at step 12 a binary number is inputted then the process continues to step 14. With CVD, the 32-bit binary number is defined as d1d2d3d4d5d6d7d8, where d1d2, . . . d8 are hexadecimal digits. After the binary number is inputted at step 12, the number of leading zeroes is determined at step 14. The number of leading zeroes is used to determine the number N of multiplications needed. N is determined form the equation N=ceil(Number of significant digits/3)−1. Ceil is a mathematical ceiling function that rounds up fractions to a full integer. In the case where CVD is used, the binary number is divided into three 12-bit parts designated $X_0$, $X_1$ and $X_2$. At step 16 the three 12-bit segments, $X_0$, $X_1$ and $X_2$ containing binary coded decimals (composed of hexadecimal numbers) are calculated then the process continues to step 18. For example, $X_0$ is calculated as: $X_0=(d6d7d8)_{10}$. $X_1$ is calculated as: $X_1=(d3d4d5)_{10}$. Similarly, $X_2$ is calculated as: $X_2=(0d1d2)_{10}$. The decimal result is defined as $Y_{cvd}$ and is calculated as shown below:

$$Y_{cvd}=((X_2 \times 2^{12}+X_1 \times 2^{12})+X_0).$$

At step 16 following the calculations for determining $X_0$, $X_1$ and $X_2$, the result (res) is given the value 0 then the process continues to step 18. At step 16 an inquiry is made to determine if N=5 if so then the variable referred to as "spec" is set to 1 and the process continues to step 18. The variable spec indicates a special case where five multiplications are needed. If five multiplications are needed, then a long multiplication process is used because the number of resulting bits exceeds hardware constraints (e.g., 64 bits). If at step 18, N is determined to be unequal to zero, flow proceeds to step 24. At step 24 the method takes $X_{N+1}$ and multiplies it by $2^{12}$ (4096) then the process continues to step 28. Step 24 is known as the short multiplication step. Short multiplication is a fast procedure that employs 4 cycles to enable quick multiplication. Short multiplication is designed for use with the current register memory constraints. The multiplication of number X by $2^{12}$ is performed by multiplying by 4096 (4000+100−4). In other words $X \times 2^{12}=(X \times 4000)+(X \times 100)−(X \times 4)$. So, $X2^{12}=4000X+100X−4X$ or $X2^{12}=4096$. The short multiplication requires 4 cycles and the steps are:

| Cycle | Operations |
| --- | --- |
| 1 | a1 = X + X; s1 = X shifted left 8 bits (i.e., s1 = 100X) |
| 2 | a2 = a1 + a1 = 4 × X |
| 3 | a3 = s1 − a2 (100*X − 4 × X); s2 = a2 shifted left 12 bits (i.e., 4000X) |
| 4 | Result = a3 + s2 (100 × X − 4 × X + 4000 × X) |

At step 28 the new res is calculated as: res=res+$X_N$ then the process continues to step 30. At step 30 the method decrements the number of future multiplications by 1 then the process continues to step 34 if N=0, otherwise the process continues to step 20. At step 20 inquiry is made to determine whether N=1 and the spec=1 then the process continues to step 24 if N is not equal to 1 or spec is not equal to 1 the afore stated process is repeated. However, if N=1 and spec=1 the process continues to step 22. At step 22 the res is calculated by multiplying $X_{N+1}$ by $2^{12}$ (4096) 22. Long multiplication is necessary in this invention when the number being converted exceeds 64 bits. After calculating the long multiplication the process continues to step 28. As with short multiplication, the new res must be calculated at step 28, the number of multiplications are decremented in step 30, and the value of N is determined in step 32. As discussed, the short multiplication process, the long multiplication process continues until N equals 0 in step 32.

Similarly, the process for calculating CVDG is identical to that of CVD except the conversion is from an input source of a 64-bit binary number and it is converted to a 128-bit decimal number. Subsequently, the hexadecimal numbers are designated as: $X_0$, $X_1$, $X_2$, $X_3$, $X_4$ and $X_5$. The binary coded decimals correspond to the particular hexadecimal numbers, and are calculated as follows: $X_0=(d14d15d16)_{10}$; $X_1=(d11d12d13)_{10}$; $X_2=(d8d9d10)_{10}$; $X3=(d5d6d7)_{10}$; $X_4=(d2d3d4)_{10}$ and $X_5=(00d1)_{10}$. The decimal result, defined as $Y_{cvdg}$ is calculated as shown below:

$$Y_{cvdg}=(((X_5 \times 2^{12}+X4 \times 2^{12}+X_3) \times 2^{12}+X_2) \times 2^{12}+X_1) \times 2^{12}+X_0.$$

Figure 2:
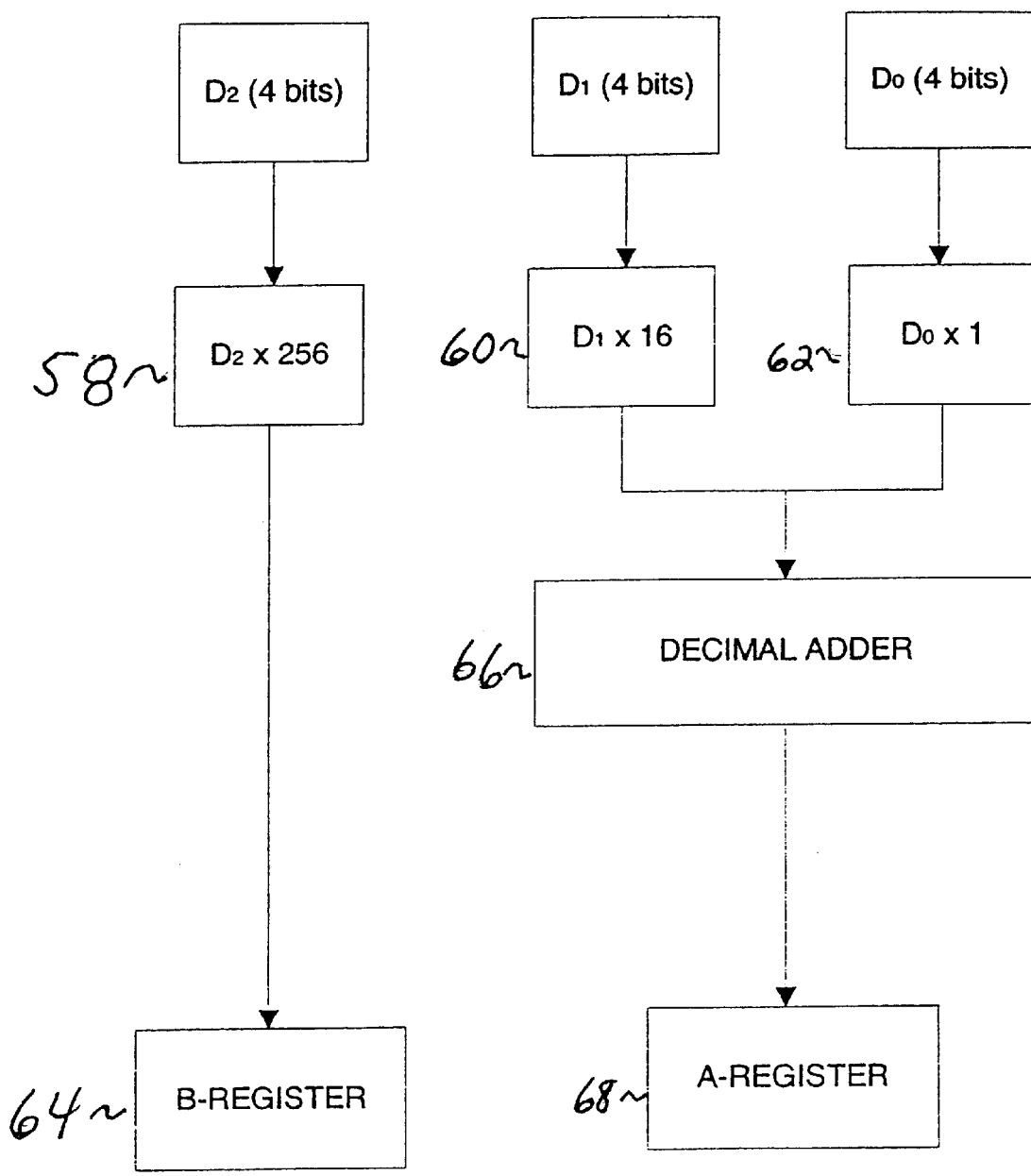
FIG. 2 is an exemplary block diagram of conversion of binary digits to binary coded decimal numbers.

FIG. 2 is an exemplary process diagram of the first stage of the 12-bit binary to decimal conversion for the preferred embodiment of the invention. In FIG. 2 the process is illustrated from the point immediately after the 32-bit binary number is divided into three 12-bit segments. Each of the 12-bit binary numbers are divided into 4-bit sub-segments (hex digits) and are referred to as $D_0$, $D_1$ and $D_2$. Do is inputted and multiplied by 1 through a look-up table 62. Through look-up table 62, $D_0$ is converted to a binary coded decimal value and the result is provided to an adder 66. Simultaneously, $D_1$ is inputted and multiplied by 16 through a look-up table 60. Through look-up table 60, $D_1$ is converted to a binary coded decimal value and the result is provided to adder 66. Adder 66 sums the result from look-up tables 62 and 60 and provides the sum to register 68. Concurrently, $D_2$ is inputted and multiplied by 256 through a look-up table 58. Through look-up table 58, $D_2$ is converted to a binary coded decimal value and the result is provided to a register 64. The A-register 68 and B-register 64 can then be added. FIG. 3 depicts exemplary tables that include the values for the three 12-bit binary to decimal conversions.

The present invention may be implemented in the form of computer-implemented processes and apparatuses for practicing those processes. The present invention can also include embodiments in the form of computer program code containing instructions embodied in tangible media, such as floppy diskettes, D-ROMs, hard drives, or any other computer-readable storage medium, wherein, when the computer program code is loaded into and executed by a processor, the processor becomes an apparatus for practicing the invention. The present invention can also include embodiments in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications to the above calculation may be made to adapt a particular situation or material to the teachings of the invention without departing from the essential scope thereof. Therefore, it is intended that the invention will include all embodiments falling within the scope of the appended claims.

What is claimed is:

1. A method for converting a number from binary to decimal, the method comprising:

obtaining an N-bit binary number;

determining a number of multiplications in response to a number of leading zeroes in said N-bit binary number;

dividing said N-bit number into 12-bit segments;

representing each 12-bit segment as a binary coded decimal number;

multiplying at least one binary coded decimal number by a variable in response to said number of multiplications; and determining a decimal result in response to said multiplying.

2. The method of claim 1 wherein said binary coded decimal number includes three binary coded decimal numbers: $X_0$, $X_1$, and $X_2$ determined utilizing the following formulas:

$$X_0=(d6d7d8)_{10}; X_1=(d3d4d5)_{10}; \text{ and } X_2 =(0d1d2)_{10}$$

where d1, d2, . . . d8 are hexadecimal numbers.

3. The method of claim 1 wherein said variable is $2^{12}$.

4. The method of claim 1 wherein said multiplying said binary coded decimal number by said $2^{12}$ is determined by the formula $$X \cdot 4000+X \cdot 100-X4,$$

where X is said binary coded decimal number.

5. The method of claim 2 wherein said decimal result is determined utilizing the following formula $$Y_{cvd}=((X_2 \times 2^{12}+X_1 \times 2^{12})+X_0)$$

where $Y_{cvd}$ equals the decimal result.

6. The method of claim 1 wherein said binary coded decimal number includes five binary coded decimal numbers: $X_0$, $X_1$, $X_2$, $X_3$, $X_4$ and $X_5$, determined utilizing the following formulas:

$$X_0=(d14d15d16)_{10}; X_1=(d11d12d13)_{10}; X_2=(d8d9d10)_{10};$$
$$X_3=(d5d6d7)_{10}; X_4=(d2d3d4)_{10} \text{ and } X_5=(00d1)_{10}$$

where d1,d2, . . . d16 are hexadecimal numbers.

7. The method of claim 6 wherein said decimal result is determined utilizing the following formula:

$$Y_{cvdg}=(((X_5 \times 2^{12}+X_4 \times 2^{12}+X_3) \times 2^{12}+X_2) \times 2^{12}+X_1) \times 2^{12}+X_0$$

where $Y_{cvdg}$ equals the decimal result.

8. A storage medium encoded with machine-readable computer program code for converting a number from binary to decimal, the storage medium including instructions for causing a processor to implement a method comprising:

obtaining an N-bit binary number;

determining a number of multiplications in response to a number of leading zeroes in said N-bit binary number;

dividing said N-bit number into 12-bit segments;

representing each 12-bit segment as a binary coded decimal number;

multiplying at least one binary coded decimal number by a variable in response to said number of multiplications; and determining a decimal result in response to said multiplying.

9. The storage medium of claim 8 wherein said binary coded decimal number includes three binary coded decimal numbers: $X_0$, $X_1$ and $X_2$ determined utilizing the following formulas:

$$X_0=(d6d7d8)_{10}; X_1=(d3d4d5)_{10}; \text{ and } X_2=(0d1d2)_{10}$$

where d1,d2, . . . d8 are hexadecimal numbers.

10. The storage medium of claim 8 wherein said variable is $2^{12}$.

11. The storage medium of claim 8 wherein said multiplying said binary coded decimal number by said $2^{12}$ is determined by the formula $$X \cdot 4000 + X \cdot 100 - X4,$$

where X is said binary coded decimal number.

12. The storage medium of claim 9 wherein said decimal result is determined utilizing the following formula:

$$Y^{cvd}=((X_2 \times 2^{12}+X_1 \times 2^{12})+X_0)$$

where $Y_{cvd}$ equals the decimal result.

13. The storage medium of claim 8 wherein said binary coded decimal number includes five binary coded decimal numbers: $X_0$, $X_1$, $X_2$, $X_3$, $X_4$ and $X_5$ determined utilizing the following formulas:

$$X_0=(d14d15d16)_{10}; X_1=(d11d12d13)_{10}; X_2=(d8d9d10)_{10};$$
$$X_3=(d5d6d7)_{10}; X_4=(d2d3d4)_{10} \text{ and } X_5=(00d1)_{10}$$

where d1,d2, . . . d16 are hexadecimal numbers.

14. The storage medium of claim 13 wherein said decimal result is determined utilizing the following formula:

$$Y_{cvdg}=(((X_5 \times 2^{12}+X_4 \times 2^{12}+X_3) \times 2^{12}+X_2) \times 2^{12}+X_1) \times 2^{12} X_0$$

where $Y_{cvdg}$ equals the decimal result.

* * * * *

UNITED STATES PATENT AND TRADEMARK OFFICE
CERTIFICATE OF CORRECTION

PATENT NO. : 6,369,725 B1
DATED : April 9, 2002
INVENTOR(S) : Busaba

It is certified that error appears in the above-identified patent and that said Letters Patent is hereby corrected as shown below:

Column 3,
Line 36, after "$D_2$" delete "Do" and insert therefor -- $D_0$ --.

Column 6,
Line 8, after "formula" delete "$Y^{cud}$" and insert therefor -- $Y_{cud}$ --.

Signed and Sealed this

Sixth Day of September, 2005

JON W. DUDAS
*Director of the United States Patent and Trademark Office*